United States Patent
Madabhushi et al.

(10) Patent No.: US 11,017,896 B2
(45) Date of Patent: May 25, 2021

(54) RADIOMIC FEATURES OF PROSTATE BI-PARAMETRIC MAGNETIC RESONANCE IMAGING (BPMRI) ASSOCIATE WITH DECIPHER SCORE

(71) Applicants: Case Western Reserve University, Cleveland, OH (US); The Cleveland Clinic Foundation, Cleveland, OH (US)

(72) Inventors: Anant Madabhushi, Shaker Heights, OH (US); Lin Li, Cleveland Heights, OH (US); Andrei S. Purysko, Westlake, OH (US); Rakesh Shiradkar, Cleveland, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 112 days.

(21) Appl. No.: 16/395,922

(22) Filed: Apr. 26, 2019

(65) Prior Publication Data
US 2020/0000396 A1   Jan. 2, 2020

Related U.S. Application Data

(60) Provisional application No. 62/691,090, filed on Jun. 28, 2018.

(51) Int. Cl.
*G16H 30/40* (2018.01)
*G06T 7/00* (2017.01)
(Continued)

(52) U.S. Cl.
CPC ............ *G16H 30/40* (2018.01); *A61B 5/055* (2013.01); *A61B 5/4381* (2013.01);
(Continued)

(58) Field of Classification Search
CPC ........ G16H 30/40; G16H 50/20; G16H 50/30; G16H 50/70; G06T 7/11; G06T 7/0012;
(Continued)

(56) References Cited

U.S. PATENT DOCUMENTS 9,779,213 B2 * 10/2017 Donovan ............... G16H 50/50
10,489,908 B2 * 11/2019 Kiraly .................. G06T 7/0012
(Continued)

OTHER PUBLICATIONS

U.S. Appl. No. 16/395,904, filed Apr. 26, 2019.
Non Final Office Action dated Oct. 8, 2020 in connection with U.S. Appl. No. 16/395,904.

*Primary Examiner* — Juan A Torres
(74) *Attorney, Agent, or Firm* — Eschweiler & Potashnik, LLC

(57) ABSTRACT

Embodiments facilitate predicting a patient prostate cancer (PCa) DECIPHER risk group. A first set of embodiments relates to training of a machine learning classifier to compute a probability that a patient is a member of a DECIPHER low/intermediate risk group based on radiomic features extracted from bi-parametric magnetic resonance imaging (bpMRI) images. A second set of embodiments relates to classifying a patient as a member of DECIPHER low/intermediate risk group, or DECIPHER high-risk group, based on radiomic features extracted from bpMRI imagery of the patient.

18 Claims, 12 Drawing Sheets

(51) Int. Cl.
*G06T 7/11* (2017.01)
*G16H 50/20* (2018.01)
*A61B 5/055* (2006.01)
*A61B 5/00* (2006.01)
*A61N 5/10* (2006.01)
*G06K 9/62* (2006.01)
*G16H 50/30* (2018.01)

(52) U.S. Cl.
CPC .......... *A61B 5/7267* (2013.01); *A61B 5/7275* (2013.01); *A61B 5/7425* (2013.01); *A61N 5/1039* (2013.01); *G06K 9/628* (2013.01); *G06K 9/6228* (2013.01); *G06K 9/6256* (2013.01); *G06K 9/6261* (2013.01); *G06T 7/0012* (2013.01); *G06T 7/11* (2017.01); *G16H 50/20* (2018.01); *G06K 2209/053* (2013.01); *G06T 2207/10088* (2013.01); *G06T 2207/20081* (2013.01); *G06T 2207/30081* (2013.01); *G06T 2207/30096* (2013.01); *G16H 50/30* (2018.01)

(58) Field of Classification Search
CPC . G06T 2207/30096; G06T 2207/20081; G06T 2207/30081; G06T 2207/10088; A61N 5/1039; G06K 9/6228; G06K 9/6256; G06K 9/6261; G06K 9/628; G06K 2209/053; G06K 9/6273; G01R 33/5608; A61B 5/055; A61B 5/4381; A61B 5/7267; A61B 5/7275; A61B 5/7425; A61B 2576/026; A61B 5/742
USPC ........................................................ 382/128
See application file for complete search history.

(56) References Cited

U.S. PATENT DOCUMENTS

| | | | |
|---|---|---|---|
| 2015/0176072 A1* | 6/2015 | Wang | C12Q 1/6883 |
| | | | 506/9 |
| 2015/0356730 A1* | 12/2015 | Grove | G06T 7/64 |
| | | | 382/124 |
| 2015/0368724 A1* | 12/2015 | Aharonov | C12Q 1/6886 |
| | | | 506/9 |
| 2017/0035381 A1* | 2/2017 | Madabhushi | A61B 6/5217 |
| 2017/0039737 A1* | 2/2017 | Madabhushi | A61B 5/08 |
| 2018/0240233 A1* | 8/2018 | Kiraly | G06T 7/0012 |
| 2019/0087532 A1* | 3/2019 | Madabhushi | G06K 9/4628 |
| 2019/0159745 A1* | 5/2019 | Madabhushi | G06K 9/46 |
| 2019/0287243 A1* | 9/2019 | Madabhushi | G06K 9/6286 |
| 2019/0347789 A1* | 11/2019 | Vaidya | G06K 9/0014 |
| 2019/0357870 A1* | 11/2019 | Madabhushi | G06N 20/00 |
| 2020/0063215 A1* | 2/2020 | Permuth | C12Q 1/6886 |

* cited by examiner

|         | 1         | 2          | 3          | 4          | 5          |
|---------|-----------|------------|------------|------------|------------|
| PIRADS v2 | 9(12.16%) | 12(16.22%) | 5(6.76%)   | 13(17.57%) | 35(47.30%) |
| GGG     | 8(10.81%) | 33(44.59%) | 15(20.27%) | 4(5.41%)   | 14(18.92%) |

600

| Selected Radiomic feature | Significance |
|---|---|
| T2 CoLIAGe | quantifies disorder in T2WI gradient orientations |
| ADC CoLIAGe | quantifies disorder in ADC gradient orientations |
| ADC Laws | characterizes spot and ripple texture patterns on ADC maps |
| ADC Gabor | captures filter response of ADC measurements at multiple orientations and scales[29] |

Figure 6

|          | Radiomic | GGG  | PIRADS v2 |
|----------|----------|------|-----------|
| Training | 0.94     | 0.84 | 0.80      |
| Testing  | 0.80     | 0.80 | 0.67      |

Figure 7

| Radiomic features | Lumen morphology features | morphology feature description | Spearman's correlation coefficient (R) | p value |
|---|---|---|---|---|
| T2 CoLlAGe (skewness) | Shape: invariant moment (median) | lumen shape circularity within ROI | -0.43 | 0.0028 |
| ADC CoLlAGe (kurtosis) | Graph: edge length (kurtosis) | local gland packing pattern divergence within ROI | 0.43 | 0.0013 |
| ADC Gabor (standard derivation) | Shape: Fourier descriptor (ratio) | lumen shape diversity within ROI | 0.43 | 0.0016 |

Figure 8

RADIOMIC FEATURES OF PROSTATE BI-PARAMETRIC MAGNETIC RESONANCE IMAGING (BPMRI) ASSOCIATE WITH DECIPHER SCORE

CROSS REFERENCE TO RELATED APPLICATIONS

This application claims the benefit of U.S. Provisional Patent Application No. 62/691,090 filed Jun. 28, 2018, the contents of which are herein incorporated by reference in their entirety.

FEDERAL FUNDING NOTICE

This invention was made with government support under the grant(s) 1U24CA199374-01, R01CA202752-01A1 R01CA208236-01A1, R01 CA216579-01A1, R01 CA220581-01A1, 1 C06 RR12463-01, and VA IBX004121A awarded by the National Institutes of Health. Also awards W81XWH-15-1-0558, W81XWH-16-1-0329, and W81XWH-17-PCRP-IDA awarded by the Department of Defense. The government has certain rights in the invention.

BACKGROUND

Prostate cancer (PCa) is the third most common cancer in the United States, with an estimated 31,620 deaths and 174,650 new cases in 2019. A majority of these patients will opt for either radical prostatectomy (RP) or radiation therapy (RT). It has been shown that adjuvant therapy improves disease-specific survival of PCa patients after surgery. However, the side-effects and remarkably expensive costs of these treatments warrant avoiding overtreatment and the selection of only patients who would truly benefit from adjuvant therapy.

DECIPHER is a molecular assay-based test that interrogates the expression of 22 metastasis-related RNA markers from prostate surgical specimens. DECIPHER is used to predict the likelihood of metastasis and PCa specific mortality based on expression patterns of 22 RNA markers from radical prostatectomy (RP) specimens. DECIPHER has been shown to be prognostic of PCa metastasis within five years following RP and has been incorporated in the National Comprehensive Cancer Network (NCCN) guidelines. The DECIPHER risk score achieves an accuracy of 75-83% in predicting risk of clinical metastasis and outperforms commonly used clinico-pathologic parameters. Although well validated, the DECIPHER test, like other existing molecular based tests, is expensive (approximately $3000 per test), and involves destruction of tissue.

Multi-parametric magnetic resonance imaging (mpMRI), including T2-weighted (T2WI), dynamic contrast enhanced (DCE), and diffusion-weighed imaging (DWI) sequences, may be used in PCa localization, diagnosis and risk stratification. Radiomic features, including computerized texture features extracted from radiological imagery, including mpMRI, may be employed in estimating PCa aggressiveness and even predict PCa prognosis prior to treatment. Radiomic features extracted from T2WI and apparent diffusion coefficient (ADC) maps derived from DWI may be predictive of biochemical recurrence (BCR). BCR is often considered a surrogate endpoint for more clinically significant outcome events, such as distant metastasis. However, these radiomic features have been often been criticized for being too opaque and non-intuitive in clinical application.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 6 illustrates a table illustrating DECIPHER risk associated radiomic features according to embodiments described herein.

FIG. 7 illustrates a table illustrating area under the receiver operating curve (AUC) of DECIPHER low/intermediate risk vs. high risk group predictions using logistic regression with radiomic features, GGG or PIRADs v 2, according to embodiments described herein.

FIG. 8 illustrates a table illustrating three top most correlated radiomic and morphology features according to embodiments described herein.

DETAILED DESCRIPTION

Figure 1:
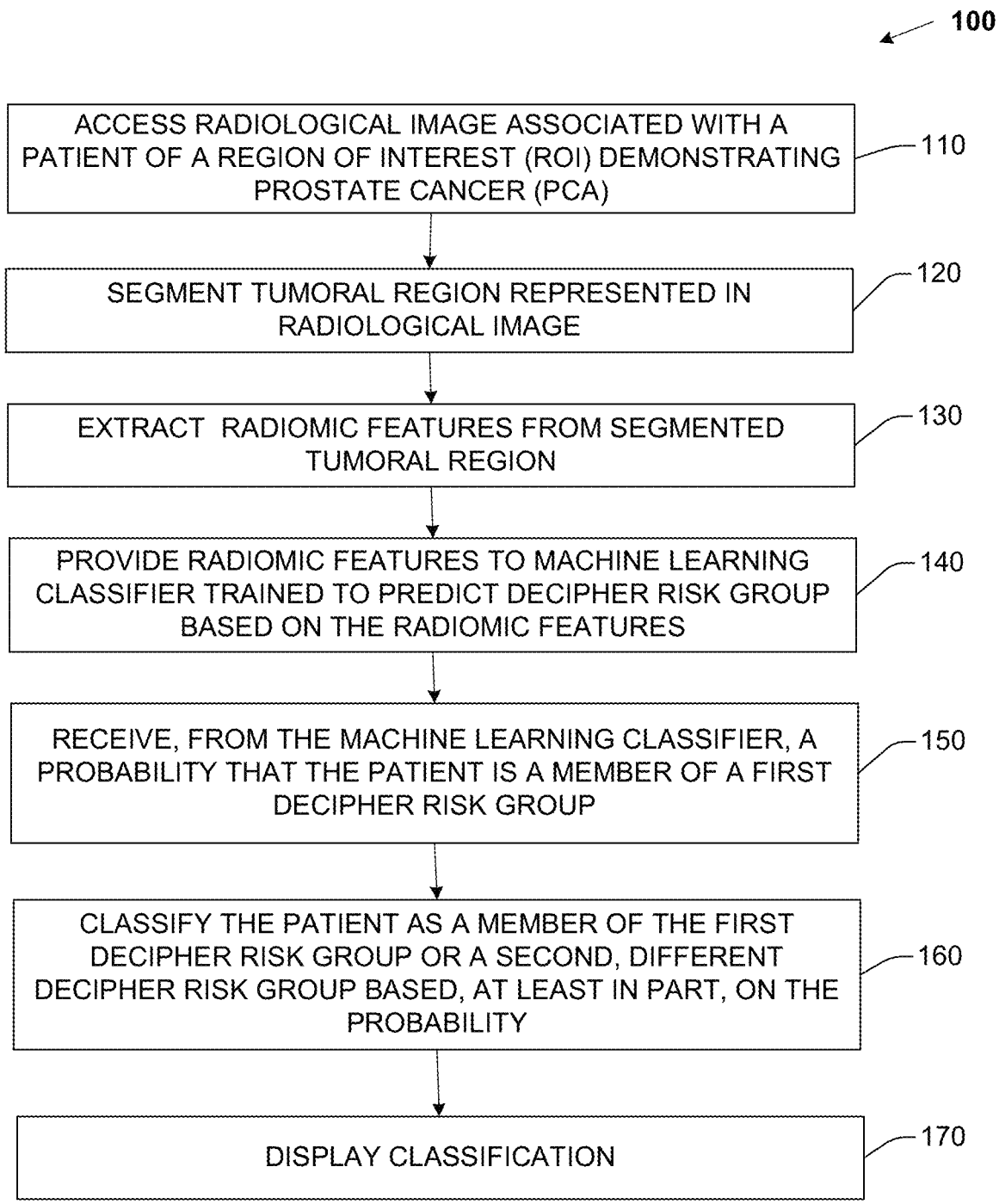
FIG. 1 illustrates a flow diagram of an example method or set of operations that employs a machine learning classifier to classify a patient demonstrating prostate cancer (PCa) according to various embodiments discussed herein.

Radiomic features extracted from pre-operative medical imagery, including magnetic resonance imaging (MRI) imagery may be employed for prostate cancer (PCa) characterization or risk-stratification in vivo. Radiomics includes the computerized extraction of and analysis of sub-visual attributes from radiographic imagery (e.g., MRI, multi-parametric MRI (mpMRI), bi-parametric MRI (bpMRI), computed tomography (CT)), and the quantification of phenotypic characteristics of a region of interest (ROI) (e.g., lesion, tumor) represented in the imagery based on the extracted features. Embodiments extract radiomic features that are predictive of DECIPHER risk score from pre-operative (e.g., pre-radical prostatectomy) MRI imagery, and generate a prognostic prediction of outcome for the patient of whom the MRI imagery is associated, based on the radiomic features. Embodiments further facilitate improved identification of PCa patients who would receive added benefit from adjuvant therapy, or who may be suitable candidates for active surveillance, compared to existing approaches.

Embodiments described herein can employ techniques discussed herein for distinguishing different DECIPHER risk groups (e.g., DECIPHER low risk score, intermediate risk score, high risk score) via a machine learning classifier trained on radiological imagery (e.g., MRI, mpMRI, bpMRI) and radiomic features extracted from said imagery that have been identified as distinguishing between different low risk, intermediate risk, or high risk lesions (e.g., tumors) according to DECIPHER risk groups. In various embodiments, radiomic features employed by various embodiments may include intratumoral and peritumoral radiomic features. Embodiments may employ intratumoral and peritumoral radiomic features that quantify heterogeneity patterns from the region of interest as an independent predictor of DECIPHER risk group. Embodiments may further employ tumoral radiomic features and peritumoral radiomic features to predict PCa prognosis or risk of clinical metastases as defined by DECIPHER risk group criteria.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Various embodiments can employ techniques discussed herein to facilitate determination of a DECIPHER risk group of a patient associated with mpMRI imagery demonstrating PCa. FIG. 1 illustrates is a flow diagram of a first example method or set of operations 100 that employs a machine learning classifier to generate a prediction of DECIPHER risk group based on radiomic features extracted from a radiological image of a patient demonstrating PCa, according to various embodiments discussed herein. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The method or set of operations 100 includes, at 110, accessing a radiological image associated with a patient. The radiological image includes a region of interest (ROI) demonstrating prostate cancer (PCa) pathology. The radiological image has a plurality of pixels, a pixel having an intensity. The radiological image may have a plurality of voxels, a voxel having an intensity. The radiological image includes a representation of a tumoral region. In one embodiment, the radiological image is a multi-parametric magnetic resonance imaging (mpMRI). The accessed radiological image (e.g., mpMRI image) can be stored in memory locally or remotely, and can be obtained via a medical imaging device one of concurrently with method 100 (e.g., via a medical imaging device implementing method 100) or prior to method 100. Accessing the radiological image (e.g., mpMRI image) includes acquiring electronic data, reading from a computer file, receiving a computer file, reading from a computer memory, or other computerized activity not practically performed in the human mind. In one embodiment, the mpMRI image is a bi-parametric MRI (bpMRI) image comprising a T2W MRI image and an apparent diffusion coefficient (ADC) map of the ROI.

The set of operations 100 also includes, at 120, segmenting a tumoral region represented in the image. Segmenting the tumoral region includes defining a tumoral boundary. In one embodiment, the tumoral region is segmented using a watershed segmentation technique, a region growing or active contour technique, or a convolutional neural network (CNN) approach. In one embodiment, the tumoral region may be segmented one of concurrently with method or operations 100 (e.g., via a medical imaging device implementing method 100) or prior to method or operations 100. Segmenting the tumoral region includes acquiring electronic data, reading from a computer file, receiving a computer file, reading from a computer memory, or other computerized activity not practically performed in the human mind.

The set of operations 100 also includes, at 130, extracting a set of radiomic features from the image. The set of radiomic features may be extracted from the tumoral region.

Extracting the set of radiomic features includes acquiring electronic data, reading from a computer file, receiving a computer file, reading from a computer memory, or other computerized activity not practically performed in the human mind. In various embodiments, the set of radiomic features may include N (N being a positive integer, e.g., 15, or a greater or lesser number) radiomic features that have been identified (e.g., via an algorithm or measure such as Pearson's correlation coefficient, minimum redundancy maximum relevance (mRMR), Wilcoxon rank sum, etc.) as the N most distinguishing or discriminating radiomic features for distinguishing a first class (e.g., DECIPHER low risk score or DECIPHER low/intermediate risk score) from a second, different class (e.g., DECIPHER high-risk score).

In one embodiment, the set of radiomic features includes fifteen (15) radiomic features. The set of radiomic features includes at least one radiomic feature extracted from the T2W MRI image and at least one radiomic feature extracted from the ADC map. In one embodiment, the set of radiomic features includes at least one ADC co-occurrence of local anisotropic gradient orientations (CoLIAGe) feature, at least one ADC Laws features, at least one ADC Gabor feature, and at least one T2WI CoLIAGe feature. ADC CoLIAGe features quantify ADC gradient heterogeneity within cancer lesion regions. ADC Laws features capture the spot and ripple texture pattern of cancer lesion ADC signals. ADC Gabor features capture the cancer lesion ADC appearance at multiple orientations. A T2WI CoLIAGe feature quantifies the local T2WI intensity gradient changes of the lesion represented in the image. In another embodiment, the set of radiomic features may include other, different radiomic features or first order statistics associated with the members of the set of radiomic features.

The set of operations 100 also includes, at 140, providing the set of radiomic features to a machine learning classifier. The machine learning classifier is trained to distinguish a first class from a second, different class based on the set of radiomic features. In one embodiment, the first class is DECIPHER low risk or DECIPHER low/intermediate risk, and the second class is DECIPHER high risk. In one embodiment, membership in the first class (DECIPHER low/intermediate risk) corresponds to a DECIPHER risk score (DS) ranging from 0 to <=0.6, while membership in the second class (DECIPHER high risk) corresponds to a DS>0.6. In another embodiment, membership in the first class (DECIPHER low risk) corresponds to a DECIPHER risk score (DS) ranging from 0 to <=0.45, and membership in the second, different class corresponds to a DS>0.45. In another embodiment, other, different classification schemes may be employed.

In one embodiment, the machine learning classifier is a logistic regression model machine learning classifier. In another embodiment, the machine learning classifier is quadratic discriminant analysis (QDA) classifier, a support vector machine (SVM) classifier, a linear discriminant analysis (LDA) classifier, a random forests (RF) classifier, or a deep learning classifier, including a convolutional neural network (CNN). In one embodiment, the set of operations 100 further includes computing first order statistics associated with each of the members of the set of radiomic features, respectively. Providing the set of radiomic features may, in this embodiment, include providing the first order statistics to the machine learning classifier. Providing the set of radiomic features to the machine learning classifier includes acquiring electronic data, reading from a computer file, receiving a computer file, reading from a computer memory, or other computerized activity not practically performed in the human mind.

The set of operations 100 also includes, at 150, receiving, from the machine learning classifier, a probability that the patient associated with the image is a member of a first DECIPHER risk group (e.g., DECIPHER low risk, DECIPHER low/intermediate risk). The machine learning classifier computes the probability based on the set of radiomic features. In one embodiment, the machine learning classifier computes the probability based on the set of radiomic features and the first order statistics. Receiving the probability from the machine learning classifier includes acquiring electronic data, reading from a computer file, receiving a computer file, reading from a computer memory, or other computerized activity not practically performed in the human mind.

The set of operations 100 also includes, at 160, classifying the patient as a member of a first DECIPHER risk group or a second, different DECIPHER risk group based, at least in part, on the probability. In various embodiments, the classification may include one or more of a most likely outcome (e.g., as determined based on the radiomic features, etc.) such as metastasis; a probability or confidence associated with a most likely outcome; and/or associated probabilities/confidences associated with each of a plurality of outcomes (e.g., low-risk of PCa metastasis, intermediate-risk of PCa metastasis, high-risk of PCa metastasis). For example, in one embodiment, generating the classification includes classifying the patient associated with the ROI as DECIPHER low/intermediate risk group when the probability is >=0.5, or classifying the patient as DECIPHER high risk group when the probability is <0.5. In this embodiment, a classification of DECIPHER low/intermediate risk group corresponds with a DECIPHER DS of <=0.6, while a classification as DECIPHER high risk group corresponds with a DECIPHER DS of >0.6. In another embodiment, other classification schemes may be employed. In one embodiment, the classification is generated with an AUC of at least 0.8.

The set of operations 100 further includes, at 170, displaying the classification. In one embodiment, the set of operations 100 includes, at 170, displaying the classification and optionally displaying one or more of the set of radiomic features, the probability, or the image. Displaying the classification and optionally displaying one or more of the set of radiomic features, the probability, or the image may include displaying the classification and optionally displaying one or more of the set of radiomic features, the probability, or the image on a computer monitor, a smartphone display, a tablet display, or other displays. Displaying the classification and optionally displaying one or more of the set of radiomic features, the probability, or the image can also include printing the classification and optionally displaying one or more of the set of radiomic features, the probability, or the image. Displaying the classification and optionally displaying one or more of the set of radiomic features, the probability, or the image can also include controlling a PCa metastasis risk prediction system, a DECIPHER risk group prediction system, a personalized medicine system, a monitor, or other display, to display operating parameters or characteristics of a machine learning classifier, during at least one of training and testing of the machine learning classifier, or during clinical operation of the machine learning classifier. By displaying the classification and optionally displaying one or more of the set of radiomic features, the probability, or the image, example embodiments provide a timely and intuitive way for a human medical practitioner to more accurately predict risk of PCa metastasis, to more accurately classify an ROI or a patient associated with the ROI into a DECIPHER risk group, classify PCa, or stratify PCa metastasis risk, thus improving on existing approaches to predicting PCa risk of metastasis, or of classifying a patient or ROI into a DECIPHER risk group. By displaying the classification and optionally displaying one or more of the set of radiomic features, the probability, or the image, example embodiments may further provide a timely and intuitive way for a human medical practitioner to more accurately identify PCa patients who would receive added benefit from adjuvant therapy, or who may be suitable candidates for active surveillance. Embodiments may further display operating parameters of the machine learning classifier.

Figure 2:
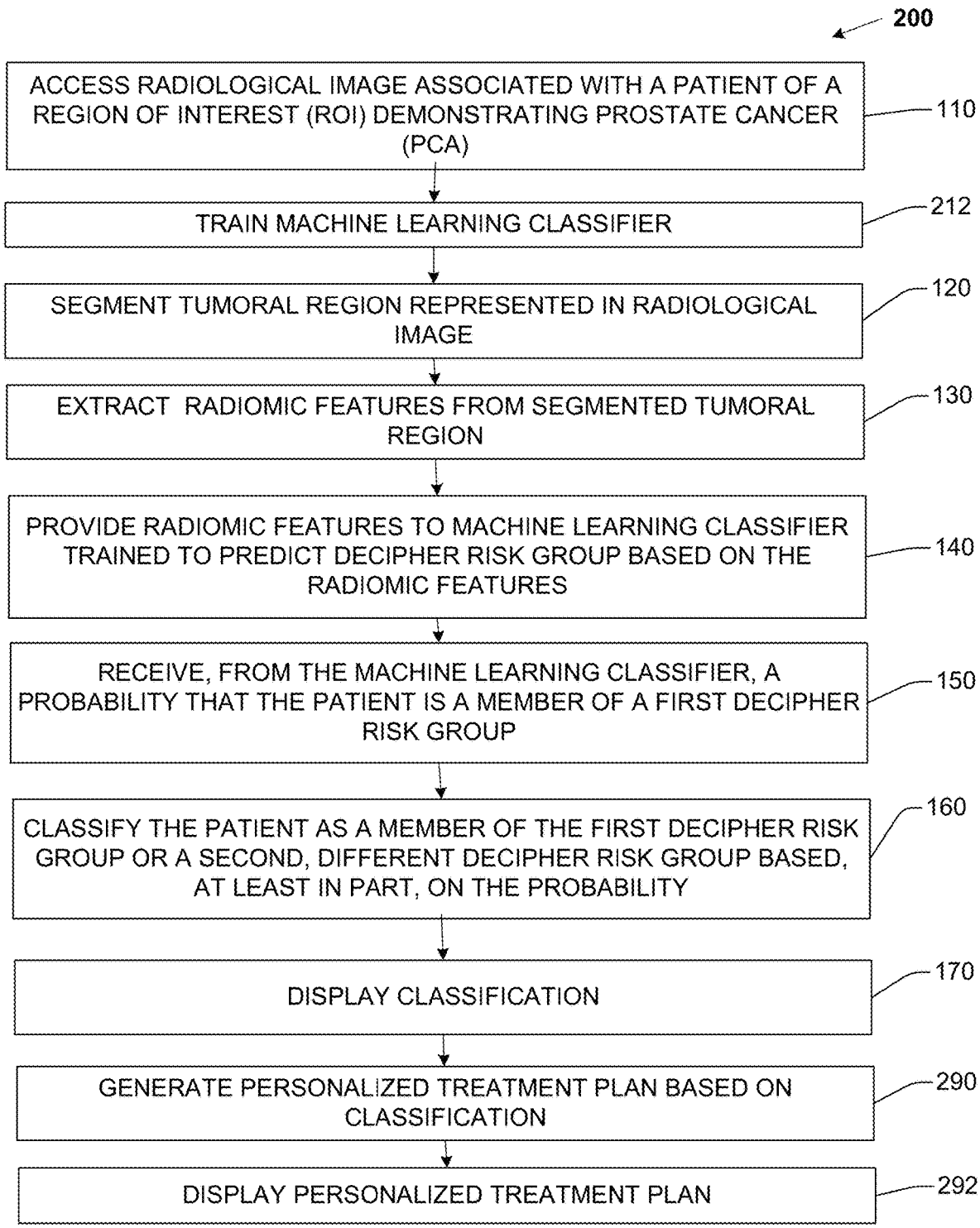
FIG. 2 illustrates a flow diagram of an example method or set of operations that employs a machine learning classifier to classify a patient demonstrating PCa according to various embodiments discussed herein.

FIG. 2 illustrates a set of operations 200 that is similar to operations 100 and includes operations 110-170 as described herein, but that includes additional operations. Operations 200 also includes, at 212, training the machine learning classifier.

Figure 3:
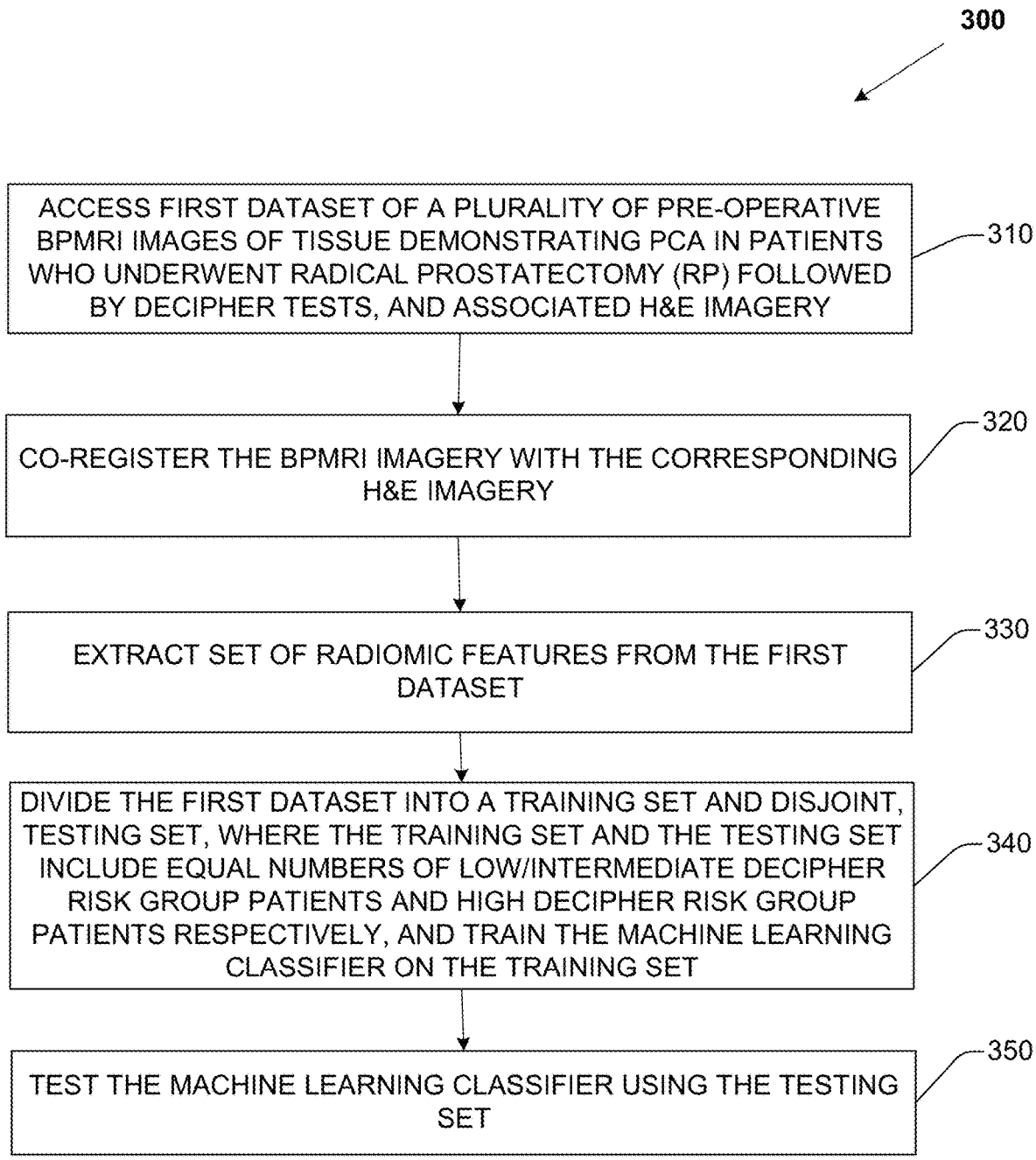
FIG. 3 illustrates a flow diagram of an example method or set of operations for training a machine learning classifier according to various embodiments discussed herein.

FIG. 3 illustrates a diagram showing an example flow of a method or set of operations 300 that facilitates training of a machine learning classifier to generate a probability that a patient associated with an ROI demonstrating PCa has a low-risk of metastasis, intermediate-risk of metastasis, or high-risk of metastasis, as defined by the DECIPHER risk score, based on radiomic features extracted from radiographic (e.g., MRI, mpMRI, bpMRI) image(s), according to various embodiments discussed herein. The set of operations 300 may include, at 310, accessing a first dataset. The first dataset includes pre-operative (e.g., pre-radical prostatectomy) mpMRI or bpMRI images of tissue demonstrating PCa in patients who underwent radical prostatectomy (RP) followed by DECIPHER tests. In one embodiment, the first dataset includes bpMRI images acquired of seventy PCa patients who underwent RP followed by DECIPHER tests. In this embodiment, a bpMRI image includes a T2W MRI image of a region of tissue demonstrating PCa, and an ADC map of the region of tissue. The first dataset further includes, for each bpMRI image, a hematoxylin and eosin (H&E) stained images of the region of tissue represented in the bpMRI image. As explained in greater detail herein, the first dataset may include a plurality of mpMRI or bpMRI images and associated H&E images comprising a positive set that is associated with a first classification (e.g., DECIPHER low-risk/intermediate risk group) and a negative set that is associated with a different second classification (e.g., DECIPHER high-risk group). The DECIPHER score (DS), ranging from 0 to 1, was used to categorize patients into low (DS<=0.45), intermediate (0.45<DS<=0.6) and high (DS>0.6) risk groups.

In one embodiment, accessing the first dataset may further include accessing or computing Gleason Grade Grouping (GGG) and Prostate Imaging Reporting and Data System version 2 (PIRADS v2) interpretation of all the patients represented in the training dataset.

Operations 300 also includes, at 320, co-registering the bpMRI imagery with the corresponding H&E imagery. H&E slices with annotated cancer lesions may be registered to the MRI imagery ensuring spatial correspondence between MRI imagery and molecular information. Digitally scanned H&E slices may be collected in quadrants and stitched into pseudo-whole mount pathology slices. In one embodiment, stitched pseudo-whole mount pathology slices are converted to grayscale, padded, and downsampled to match the resolution of the reference T2WI imagery.

In one embodiment, co-registering the bpMRI imagery with the corresponding H&E imagery further include segmenting the prostate capsule on T2WI. In one embodiment, an automated segmentation technique is employed. In another embodiment, the prostate capsule is manually segmented. In another embodiment, the prostate capsule has already been segmented.

In one embodiment, co-registering the bpMRI imagery with the corresponding H&E imagery may further include mapping lesion annotations from pathology imagery to MRI imagery. In one embodiment, multi-scale spectral embedding registration is employed to map lesion annotations from pathology images (e.g., H&E stained imagery) onto T2WI imagery. This approach includes calculating the alternative representations of the reference and template images to drive the optimal transformation.

In one embodiment, co-registering the bpMRI imagery with the corresponding H&E imagery may further include employing non-rigid registration to map lesion annotations from the T2WI imagery onto the corresponding ADC maps. For example, in one embodiment, the Elastix toolbox, or other medical image registration technique, may be employed to non-rigidly register annotations from the T2WI imagery onto the corresponding ADC maps. In another embodiment, other non-rigid registration techniques may be employed.

The set of operations 300 also includes, at 330, extracting radiomic features from the bpMRI imagery. In one embodiment, seventy-five (75) radiomic features, including first-order statistics (n=10), Gabor (n=14), Haralick (n=13), Laws (n=25) and Co-occurrence of Local Anisotropic Gradient Orientations (CoLIAGe) (n=13), are derived from both T2WI and ADC maps. These radiomic features are extracted on a voxel-wise basis within the tumor regions of interest (ROIs) obtained via co-registration. In one embodiment, T2WI signal intensity for each patient is standardized prior to feature extraction to the template intensity distribution to keep the T2WI intensity range consistent.

The set of operations 300 also includes, at 340, training the machine learning classifier. In one embodiment, the machine learning classifier includes a logistic regression model. In one embodiment, low/intermediate (N=48 lesions, D1) and high risk groups (N=26 lesions, D2) are evenly split into a training set (ND1=24, ND2=13) and a hold-out testing set (ND1=24, ND2=13). In this embodiment, radiomic features are extracted from lesion ROIs and distribution statistics are calculated for each ROI. In one embodiment, Pearson's correlation coefficient (R)>0.6 is used as the criterion to discard highly correlated radiomic features. In this embodiment, the remainder of the radiomic features (R<=0.6) are employed to train the logistic regression model with elastic-net regularization via a 5-fold cross validation approach. In one embodiment, the selection of features that discriminate D1 and D2 is performed simultaneously with the training of the predictive model (e.g., machine learning classifier). Embodiments may generate a receiver operating characteristic curve (ROC) and calculate an associated area under the ROC (AUC).

In another embodiment, training a machine learning classifier may include training another, different type of machine learning classifier, (e.g., QDA (Quadratic Discriminant Analysis classifier), SVM (Support Vector Machine), LDA (Linear Discriminant Analysis) classifier, DLDA (Diagonal Line Discriminant Analysis) classifier, RF (Random Forest) classifier, CNN (Convolutional Neural Network) classifier, etc.) based on the training set, and, for each image in the training dataset, the values of the N radiomic features for that image, and a known outcome or classification (e.g., PCa metastasis, non-metastasis, DECIPHER risk group) associated with that image. Based on the training set, and, for each image in the training set, the values of the N radiomic features for that image, and a known outcome or classification (e.g., PCa metastasis or non-metastasis, DECIPHER risk group) associated with that image, the classifier can determine classes for PCa DECIPHER risk group, and probability of PCa DECIPHER risk group membership for associated feature vectors (e.g., comprising N values of radiomic features). In one embodiment, the classifier is additionally trained with the first order statistical values computed for each of the N most distinguishing radiomic features.

While Pearson's correlation coefficient is described herein as one technique for discarding highly correlated radiomic features, in another embodiment, other feature selection techniques may be employed. For example, operations 300 may further include, at 340, determining, for each image in the first dataset, values for that image for each of the N (N being a positive integer, e.g., 15) most distinguishing radiomic features for predicting PCa DECIPHER risk. The N most distinguishing radiomic features can be determined via any of a variety of algorithms or measures (e.g., Pearson's correlation coefficient, random forest (RF), t-test, Wilcoxon, mRMR, etc.). In one embodiment, N has a value of fifteen, while in another embodiment, N has another, different positive value. In one embodiment, first order statistical values may be computed for each of the N most distinguishing radiomic features.

In one embodiment, operations 300 may optionally include, at 350, testing the machine learning classifier on the held-out testing set. Testing the machine learning classifier may include determining if the trained model (e.g., the logistic regression model) is robust. In one embodiment, 10-fold cross validation was applied to avoid overfitting. In this embodiment, least absolute shrinkage and selection operator (Lasso) regularization may be integrated with the logistic regression model to select the DECIPHER risk associated features. The median of the selected feature coefficients across the 10-fold cross validation are computed and may be adopted to build the final trained model. Embodiments may employ analysis of variance (ANOVA) to assess whether a machine learning classifier and radiomic features as described herein add significant predictive value over GGG and PIRADS-v2. In this manner, the ability of embodiments employing the machine learning classifier as described herein to correctly classify MRI imagery, including mpMRI or bpMRI images of tissue demonstrating PCa, can be tuned and/or estimated.

Training the machine learning classifier can also include determining which radiomic features are most discriminative in distinguishing DECIPHER risk group in PCa. Training the machine learning classifier can also include determining the optimal combination of parameters used in the computation of the probability that can best separate a positive class from a negative class (e.g., DECIPHER low/intermediate risk group or DECIPHER high-risk group).

Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining the optimal combination of parameters used in the computation of a probability of PCa metastasis risk (e.g., which radiomic features to extract, number of radiomic features to extract) to best separate a positive and negative class. In one embodiment, the machine learning classifier is trained until an AUC=0.8 is achieved.

Returning to FIG. 2, the set of operations 200 may further include, at 290, generating a personalized PCa treatment plan. The personalized PCa treatment plan may be generated based, at least in part, on the classification and optionally on one or more of the set of radiomic features, the probability, or the image. The personalized PCa treatment plan may be generated for the patient of whom the image was acquired based, at least in part, on the classification and optionally on one or more of the set of radiomic features, the probability, or the image. Defining a personalized PCa treatment plan facilitates delivering a particular treatment that will be therapeutically active to the patient, while minimizing negative or adverse effects experienced by the patient. For example, the personalized PCa treatment plan may suggest a surgical treatment, may define a pharmaceutical agent dosage or schedule, may suggest a patient as a candidate for active surveillance, and/or other recommendations for PCa management, for a patient, wherein the specific recommendation can depend on a DECIPHER risk group associated with the patient. Generating the personalized PCa treatment plan includes acquiring electronic data, reading from a computer file, receiving a computer file, reading from a computer memory, or other computerized activity not practically performed in the human mind.

The set of operations 200 can further comprise, at 292, displaying the personalized PCa treatment plan according to embodiments described herein.

Techniques and aspects of various embodiments are further explained below, in connection with an example embodiment that facilitates determination of a PCa DECIPHER risk group for a patient represented in radiological imagery including bpMRI imagery.

Example Use Case: Radiomic Features Derived from Pre-Operative mpMRI of PCa Facilitate Prediction of DECIPHER Risk Score.

Figure 4:
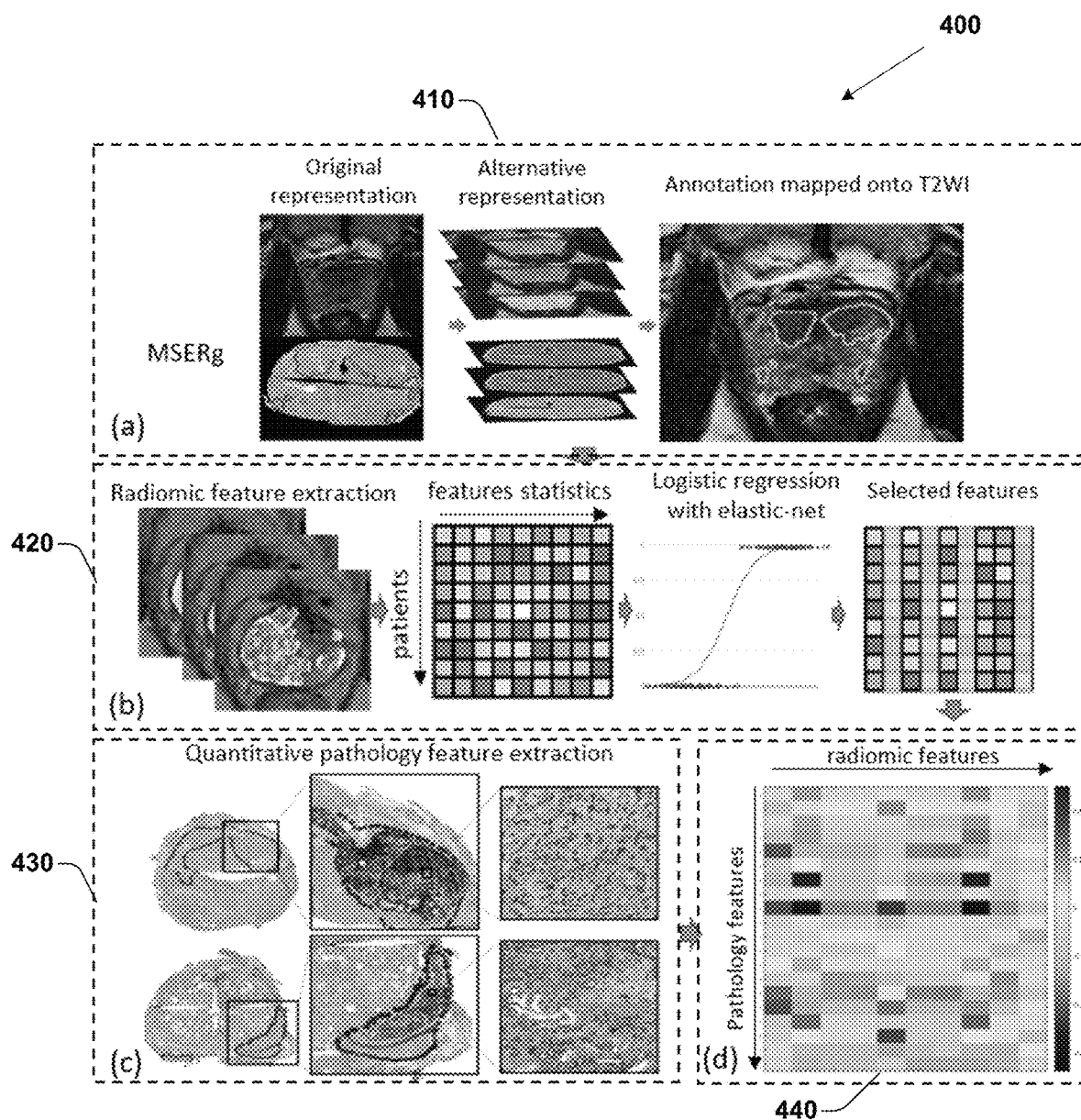
FIG. 4 illustrates a workflow diagram of examples described herein.

An example embodiment included training a machine learning classifier to predict DECIPHER risk groups in PCa independently of clinical parameters, based on example cases of low-risk, intermediate risk, and high-risk lesions (e.g., tumors). FIG. 4 is a workflow diagram of an example methodology or operations 400 according to embodiments described herein. In this example, a retrospective, Institutional Review Board (IRB)-approved and HIPAA compliant study included 70 PCa patients who underwent RP followed by DECIPHER tests at a single center (e.g., institution). Pre-operative 3T T2WI and ADC maps were reviewed by a board certified radiologist with fellowship training in abdominal imaging and 7 years of experience in prostate imaging. The prostate specimens were sliced into quadrants, hematoxylin and eosin (H&E) stained and reviewed by a board-certified pathologist with more than ten years of experience. The H&E stained slices were digitized at 20×, with N=74 lesions annotated at peripheral zone by the pathologist. The corresponding lesions were then sampled from the tissue specimens and were sent for DECIPHER test. The DECIPHER score (DS), ranging from 0 to 1, was used to categorize patients into low (DS<=0.45), intermediate (0.45<DS<=0.6) and high (DS>0.6) risk groups.

Figure 5:
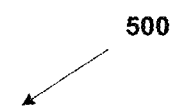
FIG. 5 illustrates a table illustrating a distribution of Prostate Imaging Reporting and Data System version 2 (PIRADS v2) and includes Gleason Grade Grouping (GGG) for lesions (N=74) considered in one example.

In addition, this example included Gleason Grade Grouping (GGG) and Prostate Imaging Reporting and Data System version 2 (PIRADS v2) interpretation of all the patients for whom the DECIPHER test had been performed. GGG is a PCa grading system, comprising of 5 groups. Group 1=Gleason score 6, group 2=Gleason score 3+4, group 3=Gleason score 4+3, group 4=Gleason score 8, and group 5=Gleason score 9. PIRADS v2 was introduced for a radiology reader to score a patient from 1 through 5 based on the patient's mpMRI phenotype, 1 suggesting that the lesion is obviously benign while 5 suggesting that the lesion is obviously malignant. The GGG and PIRADS v2 distributions for the lesions within this example are included in table 500 illustrated in FIG. 5.

In this example, mpMRI imagery (e.g., bpMRI imagery) is co-registered, at 410 with the H&E stained slices. In this example, a pathologist and radiologist, working in unison, provided spatial correspondences between MRI and associated RP slices. The H&E stained slices with cancer lesions annotated were registered to associated MRI imagery, ensuring spatial correspondence between imaging and molecular information. The digitally scanned H&E slices were collected in quadrants and stitched into pseudo-whole mount pathology slices using the HISTOSTITCHER software. In other examples, other techniques may be employed to generate pseudo-whole mount pathology slices. The stitched red-green-blue (RGB) pathology images were then converted to grayscale, padded and downsampled to about 10 µm/pixel resolution to match the resolution of the reference T2WI. In this example, the prostate capsule on T2WI was manually segmented using 3D Slicer by an expert radiologist, while in another example, automated segmentation techniques may be employed. In this example, multi-scale spectral embedding registration (MSERg), was employed to accurately map the lesion annotations from pathology images onto T2WI, while in another example, other registration techniques may be employed. The MSERg approach involves calculating the alternative representations of the reference and template images to drive the optimal transformation. Additionally, in this example, the Elastix toolbox was employed to conduct a non-rigid registration mapping the lesion annotations from T2WI onto corresponding ADC maps. Registration results were reviewed by the radiologist and edited as necessary.

In this example, at 420, radiomic features are extracted from the mpMRI imagery, including the T2WI and ADC maps. In this example, T2WI signal intensity for each patient was standardized prior to feature extraction to the template intensity distribution to keep the T2WI intensity range consistent. 75 Radiomic features, including first-order statistics (n=10), Gabor (n=14), Haralick (n=13), Laws (n=25) and Co-occurrence of Local Anisotropic Gradient Orientations (CoLIAGe) (n=13), were derived from both T2WI and ADC maps. These features facilitate detecting the presence and stratifying the risk of PCa. These radiomic features are extracted on a voxel-wise basis within the tumor ROIs obtained via co-registration.

In this example, a radiomics-based predictive model is trained. In this example, low/intermediate (N=48 lesions, D1) and high risk groups (N=26 lesions, D2) are evenly split into a training set (ND1=24, ND2=13) and a hold-out testing set (ND1=24, ND2=13). Radiomic features were extracted from lesion ROIs and their distribution statistics were calculated for each ROI. Pearson's correlation coefficient (R)>0.6 was used as the criterion to discard highly correlated radiomic features. The remainder of the radiomic features (R<=0.6) were employed to train a logistic regression model with elastic-net regularization via a 5-fold cross validation approach. This method allows for intelligent selection of features that discriminate D1 and D2 and train the predictive model simultaneously. A receiver operating characteristic curve (ROC) was generated and area under the ROC (AUC) was calculated. The trained logistic regression model was then validated on the hold-out testing set to determine if the trained model is robust and could be generalized. Analysis of variance (ANOVA) was used to assess whether embodiments employing radiomic features as described herein can add significant predictive value over GGG and PIRADS-v2.

In this example, radiomics and tissue morphology may be correlated at 440. In this example, gland segmentation within the lesion ROIs on digitized surgical specimens was first obtained using the Unet segmentation network at 10× resolution. Gland morphology features, including lumen shape, orientation, arrangement, and graph-based entropy were then extracted at 430 to characterize the PCa gland morphology. Fifteen distribution statistics including mean, standard deviation, range, minimum, maximum, mode, median, variance, kurtosis, harmonic mean, skewness, absolute deviation, inter-quartile range, disorder, min/max, were calculated for morphology features of each lesion on the digitized pathology images. Spearman's correlation coefficient was used to assess the correlation between quantitative morphology features and DECIPHER risk associated radiomic features. A two-tailed test (p<0.05) was used to test the statistical significance.

In one example, a DECIPHER risk group predictive model was trained via logistic regression in conjunction with elastic-net regularization which resulted in a set of 15 most discriminative radiomic features. Categorically, these radiomic features include: ADC CoLIAGe features, which quantify ADC gradient heterogeneity within cancer lesion regions; ADC Laws features, which capture the spot and ripple texture pattern of cancer lesion ADC signals; ADC Gabor features, which capture the cancer lesion ADC appearance at multiple orientations, and T2WI CoLIAGe features, which quantify the lesion local T2WI intensity gradient changes. FIG. 6 illustrates table 600, which illustrates more detailed explanations of extracted radiomic features.

In this example, the model resulted in a mean AUC=0.94 on the training set and AUC=0.80 in the hold-out validation set, as listed in table 700 in FIG. 7, suggesting that the selected radiomic features are strongly associated with DECIPHER risk groups. In addition, examples included training logistic regression models with clinical parameters GGG and PIRADS v2, resulting in corresponding AUCs of 0.80 and 0.67 respectively, in terms of discriminating D1 and D2 on the hold-out validation set. These results indicate that embodiments employing radiomic features as described herein provide a comparable predictive performance as GGG while outperforming PIRADS v2. It also shows that embodiments employing radiomic features as described herein add significant value to the predictive model that included GGG and PIRADS v2 according to ANOVA with p<0.05. In addition, ADC derived CoLIAGe features according to embodiments described herein may facilitate improved prediction of higher risk of BCR.

Examples demonstrate a morphological basis for DECIPHER risk correlated radiomic features. In one example, correlations between DECIPHER risk associated radiomic phenotypes and PCa morphology features derived from the lesion ROIs were demonstrated. The PCa morphology features used in this example may be associated with PCa aggressiveness and outcomes, such as BCR. Correlations between radiomic features and quantitative morphology features may provide a morphological basis of the signatures captured by radiomic features. For example, associations between PCa Gleason grade discriminating radiomic features and quantitative morphology features indicate that the Gabor feature extracted from T2WI may be correlated with gland shape features.

Figure 9:
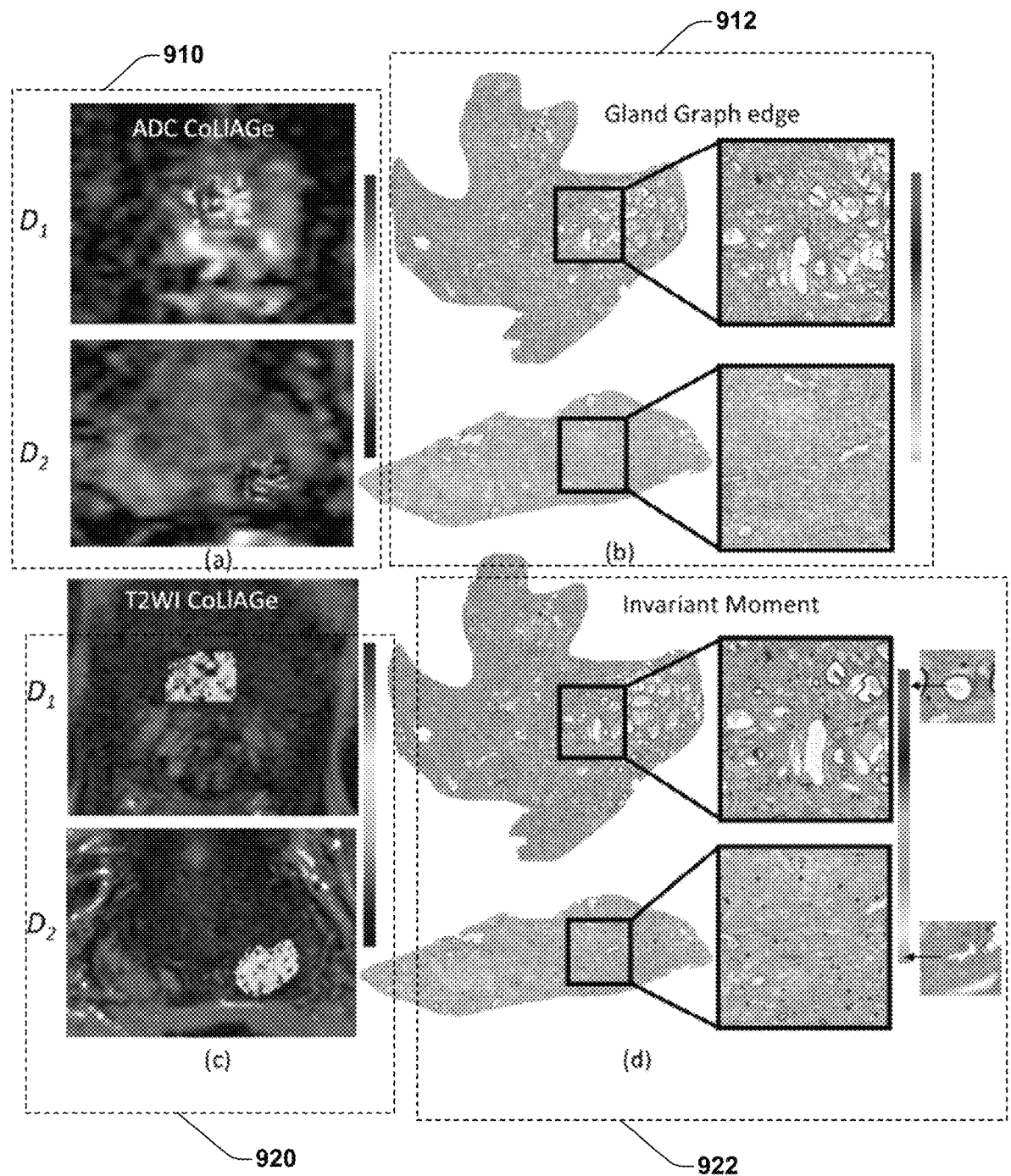
FIG. 9 illustrates two top most correlated radiomic and morphology features according to embodiments described herein.

Examples and embodiments described herein indicate that the DECIPHER risk associated radiomic features are associated with gland shape and architecture features as shown in table 800 illustrated in FIG. 8. FIG. 9 illustrates the top two most correlated pairs of correlated radiomic and gland morphology features within the D1 and D2 groups respectively. FIG. 9 illustrates, at 910, an ADC CoLlAGe feature for patients from D1 and D2. FIG. 9 illustrates, at 912, a gland morphology feature (gland edge length heterogeneity) that correlates with the radiomic feature illustrated at 910 by showing the minimal spanning tree graph, where the color map indicates the edge distance. FIG. 9 also illustrates, at 920, a T2WI CoLlAGe feature for patients from D1 and D2. FIG. 9 further illustrates, at 922, the correlated morphology feature illustrated at 920, by assigning the value of invariant moment of the lumen shape, where the color map indicates the circularity of the lumen shape. The correlation results indicate that high heterogeneity in T2WI intensities within tumor ROIs may be associated with higher convolutedness of lumen which may lead to non-uniform tissue relaxation times. Disorder in ADC measurements was correlated with gland packing and shape diversity within tumor ROIs. This indicates that water diffusion may be more chaotic (i.e., multi-directional) due to diverse gland packing architecture and thus cause an increase in the heterogeneity of ADC measurements. Radiomic feature and gland morphology feature correlations suggest that DECIPHER high risk patients tend to have more convoluted, inconsistent gland shape and heterogeneous gland packing architecture.

As demonstrated by the example embodiments, various embodiments can facilitate prediction of PCa DECIPHER risk score based on radiomic features extracted from radiological images, including bpMRI images. The ability to identify or stratify patients into PCa DECIPHER risk categories based on radiomic features extracted from bpMRI images using a machine learning classifier trained according to embodiments described herein can provide the technical improvement of facilitating improving the utility of bpMRI as a non-invasive PCa DECIPHER risk assessment tool for independent prognostic prediction of outcomes in PCa, and further as a complement to existing assays for improved identification of PCa patients who would receive additional benefit from adjuvant chemotherapy. Embodiments thus provide a measurable improvement over existing methods, systems, apparatus, or other devices in prediction of PCa DECIPHER risk score.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 100, 200, or 300, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to prediction of PCa DECIPHER risk group or prediction of PCa metastasis are based on radiomic features that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 10:
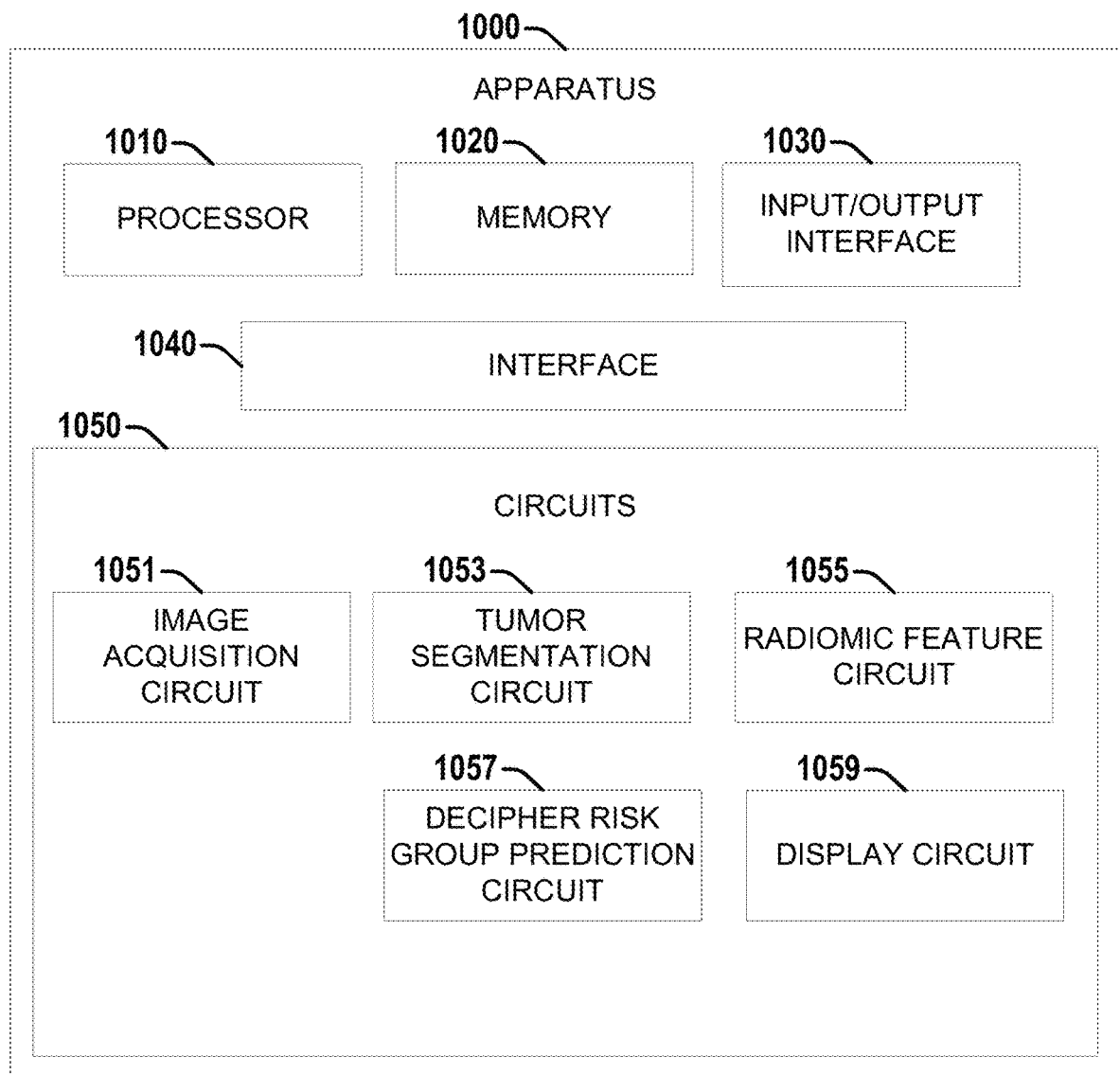
FIG. 10 illustrates a diagram of an example apparatus that can facilitate classifying a patient demonstrating PCa according to various embodiments discussed herein.

FIG. 10 illustrates an example apparatus 1000 that can facilitate predicting PCa DECIPHER risk group based on radiomic features extracted from MRI imagery, according to various embodiments discussed herein. Apparatus 1000 may be configured to perform various techniques, operations, or methods discussed herein, for example, training a machine learning classifier (e.g., logistic regression model classifier, quadratic discriminant analysis classifier, support vector machine, etc.) based on training data to determine probability of PCa DECIPHER risk group based on radiomic features extracted from MRI imagery, or employing such a trained machine learning classifier to generate a classification of PCa DECIPHER risk group (e.g., low-risk, intermediate risk, high-risk) based on radiomic features extracted from an MRI image (e.g., mpMRI, bpMRI) of a patient demonstrating PCa. In one embodiment, apparatus 1000 includes a processor 1010, and a memory 1020. Processor 1010 may, in various embodiments, include circuitry such as, but not limited to, one or more single-core or multi-core processors. Processor 1010 may include any combination of general-purpose processors and dedicated processors (e.g., graphics processors, application processors, etc.). The processor(s) can be coupled with and/or can comprise memory (e.g., memory 1020) or storage and can be configured to execute instructions stored in the memory 1020 or storage to enable various apparatus, applications, or operating systems to perform operations and/or methods discussed herein.

Memory 1020 is configured to store a bi-parametric magnetic resonance imaging (bpMRI) image associated with a patient, where the image includes a region of interest (ROI) demonstrating prostate cancer (PCa) pathology. The bpMRI image has a plurality of pixels, a pixel having an intensity. The bpMRI image includes a T2W MRI image and an apparent diffusion coefficient (ADC) map. In some embodiments, memory 1020 can store a training set of images (e.g., comprising bpMRI images showing radiomic features, along with a known DECIPHER risk group, or outcome) for training a classifier (e.g., logistic regression model classifier, etc.) to determine a probability of PCa DECIPHER risk group, while in the same or other embodiments, memory 1020 can store a radiological image of a patient for whom a prediction of PCa DECIPHER risk group or outcome is to be determined. Memory 1020 can be further configured to store one or more clinical features or other data associated with the patient of the bpMRI image. The bpMRI image may have a plurality of voxels, a voxel having an intensity.

Apparatus 1000 also includes an input/output (I/O) interface 1030; a set of circuits 1050; and an interface 1040 that connects the processor 1010, the memory 1020, the I/O interface 1030, and the set of circuits 1050. I/O interface 1030 may be configured to transfer data between memory 1020, processor 1010, circuits 1050, and external devices, for example, a medical imaging device such as an MRI system or apparatus.

The set of circuits 1050 includes image acquisition circuit 1051, tumor segmentation circuit 1053, radiomic feature circuit 1055, DECIPHER risk group prediction circuit 1057, and display circuit 1059.

Image acquisition circuit 1051 is configured to access the bpMRI image. Accessing the bpMRI image may include accessing the bpMRI image stored in memory 1020. In another embodiment accessing the bpMRI image may include acquiring electronic data, reading from a computer file, receiving a computer file, reading from a computer memory, or other computerized activity not practically performed in the human mind.

Tumor segmentation circuit 1053 is configured to segment a tumoral region represented in the bpMRI image. Segmenting the tumoral region includes defining a tumoral boundary. In one embodiment, tumor segmentation circuit 1053 is configured to automatically segment the tumoral region using a watershed segmentation technique, a region growing or active contour technique, or a convolutional neural network (CNN) approach. In another embodiment, tumor segmentation circuit 1053 may be configured to employ other, different segmentation techniques or algorithms.

Radiomic feature circuit 1055 is configured to extract a set of radiomic features from the bpMRI image. In one embodiment, the set of radiomic features includes at least one ADC co-occurrence of local anisotropic gradient (CoLIAGe) feature, at least one ADC Laws features, at least one ADC Gabor feature, and at least one T2WI CoLIAGe feature. In one embodiment, the set of radiomic features includes fifteen radiomic features, including at least one ADC CoLIAGe feature, at least one ADC Laws features, at least one ADC Gabor feature, and at least one T2WI CoLIAGe feature. In another embodiment, the set of radiomic features may include another, different number of radiomic features, or other, different radiomic features.

DECIPHER risk group prediction circuit 1057 is configured to compute a probability that the patient associated with the ROI is a member of a first DECIPHER risk group, or a member of a second, different DECIPHER risk group. DECIPHER risk group prediction circuit 1057 is configured to compute the probability based on the set of radiomic features. DECIPHER risk group prediction circuit 1057 is also configured to generate a classification of the patient as a member of the first DECIPHER risk group, or a member of the second, different DECIPHER risk group based, at least in part, on the probability. In one embodiment, DECIPHER risk group prediction circuit 1057 is configured as a logistic regression model classifier. In another embodiment, DECIPHER risk group prediction circuit 1057 is configured as another, different type of machine learning classifier including, for example, an LDA classifier, a QDA classifier, an SVM classifier, a random forest classifier, or a CNN classifier.

Display circuit 1059 is configured to display the classification. In various embodiments, the classification may include one or more of a most likely outcome (e.g., as determined based on the radiomic features) such membership in a first DECIPHER risk group or second, different DECIPHER risk group (e.g., DECIPHER low risk or low/intermediate risk, DECIPHER high risk), a probability or confidence associated with a most likely outcome; and/or associated probabilities/confidences associated with each of a plurality of outcomes. Display circuit 1059 may be further configured to optionally display the bpMRI image, the probability, the set of radiomic features, or other data associated with the patient or with the operation of apparatus 1000.

In another embodiment, radiomic feature circuit 1055 is further configured to compute first order statistics associated with each member of the set of radiomic features. In this embodiment, DECIPHER risk group prediction circuit 1057 is configured to compute the probability based on the set of radiomic features and/or the first order statistics.

Figure 11:
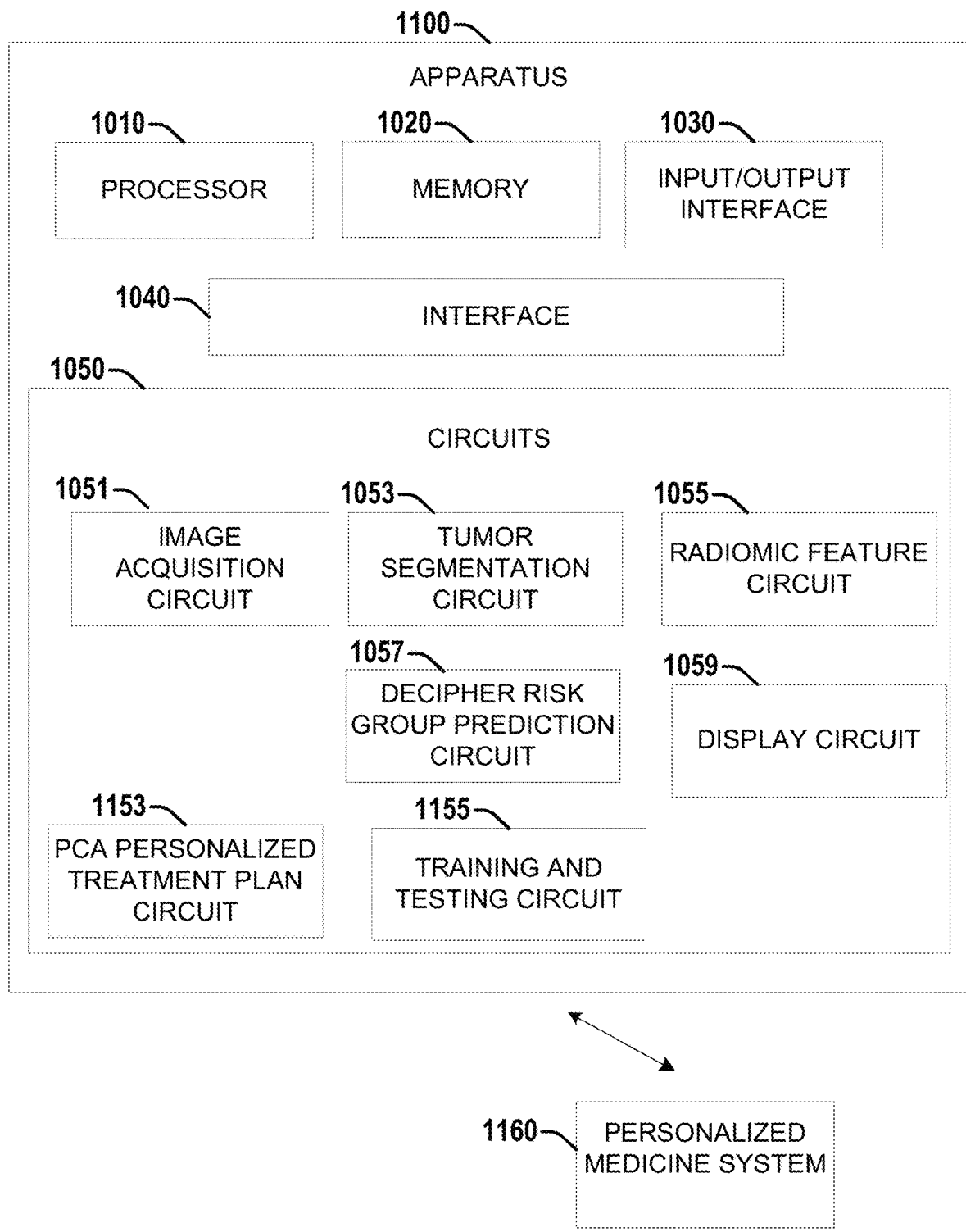
FIG. 11 illustrates a diagram of an example apparatus that can facilitate classifying a patient demonstrating PCa according to various embodiments discussed herein.

FIG. 11 illustrates an apparatus 1100 that is similar to apparatus 1000 but that includes additional elements and details. In one embodiment of apparatus 1100, the set of circuits 1050 further includes a PCa personalized treatment plan circuit 1153 configured to generate a personalized treatment plan based, at least in part, on the classification. PCa personalized treatment plan circuit 1153 may be configured to generate a personalized treatment plan based, at least in part, on a classification obtained from DECIPHER risk group prediction circuit 1057 or display circuit 1059. PCa personalized treatment plan circuit 1153 may be configured to generate a personalized treatment plan for the patient of whom the bpMRI image was acquired based, at least in part, on the classification derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, may suggest a patient for active surveillance, and/or other treatments. Generating a personalized treatment plan based on a more accurate prediction of PCa DECIPHER risk group or a more accurate prediction of metastasis risk facilitates more efficient delivery of costly therapeutic or surgical treatments to patients more likely to benefit from such treatments. For example, the personalized treatment plan may suggest a first surgical treatment, may suggest a first pharmaceutical agent dosage or schedule, may suggest a patient for active surveillance, and/or other treatments for a patient classified as DECIPHER low risk group or DECIPHER low/intermediate risk group, or may suggest a second, different surgical treatment or second, different pharmaceutical agent dosage or schedule or treatments or may suggest a patient as unsuitable for active surveillance for a patient classified as DECIPHER high-risk.

In this embodiment, display circuit 1059 is further configured to display the personalized treatment plan.

In one embodiment of apparatus 1100, the set of circuits 1050 further includes a training and testing circuit 1155. Training and testing circuit 1155 is configured to train DECIPHER risk group prediction circuit 1057 on a training cohort; and optionally test DECIPHER risk group prediction circuit 1057 on a testing cohort, according to various embodiments described herein.

In various embodiments, DECIPHER risk group prediction circuit 1057 can receive one or more radiomic features or values (including, for example, first order statistical values) for the one or more radiomic feature extracted from a bpMRI image from radiomic feature circuit 1055. In some embodiments, the received features or values of the features can correspond to an image of a training dataset, and DECIPHER risk group prediction circuit 1057 can be trained based on the values and a known PCa DECIPHER risk group associated with the image. In the same or other embodiments, the features or received values of the features can correspond to an image of a testing dataset or of a patient for whom a prediction of PCa DECIPHER risk group is to be generated, and DECIPHER risk group prediction circuit 1057 can generate a prognosis based on the radiomic feature(s) or received values.

In one embodiment, apparatus 1100 further includes personalized medicine device 1160. Apparatus 1100 may be configured to provide the probability, the classification, a personalized treatment plan, or other data to personalized medicine device 1160. Personalized medicine device 1160 may be, for example, a computer assisted diagnosis (CADx) system or other type of personalized medicine device that can be used to facilitate the prediction of DECIPHER risk group, or of PCa metastasis risk. In one embodiment, PCa personalized treatment plan circuit 1153 can control personalized medicine device 1160 to display the probability, the classification, a personalized treatment plan, or other data to on a computer monitor, a smartphone display, a tablet display, or other displays.

Figure 12:
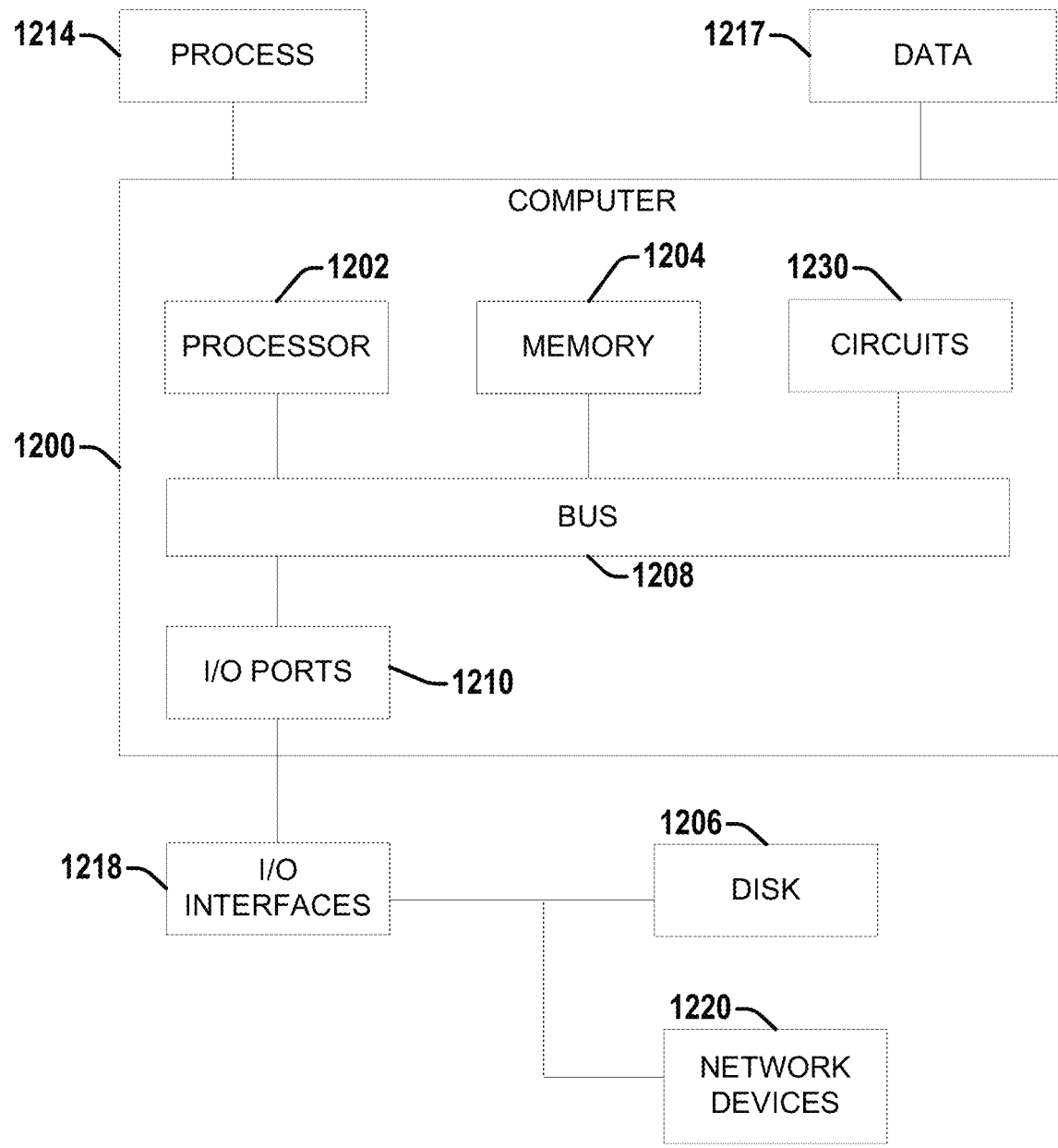
FIG. 12 illustrates a diagram of an example computer in which embodiments described herein may be implemented.

FIG. 12 illustrates an example computer 1200 in which example methods illustrated herein can operate and in which example methods, apparatus, circuits, operations, or logics may be implemented. In different examples, computer 1200 may be part of a PCa DECIPHER risk group prediction system or apparatus, a PCa tumor classification system or apparatus, a CADx system, an MRI system, a CT system, a digital whole slide scanner, or a personalized medicine system, or may be operably connectable to PCa DECIPHER risk group prediction or apparatus, a PCa tumor classification system or apparatus, a CADx system, an MRI system, a CT system, a digital whole slide scanner, or a personalized medicine system.

Computer 1200 includes a processor 1202, a memory 1204, and input/output (I/O) ports 1210 operably connected by a bus 1208. In one example, computer 1200 may include a set of logics or circuits 1230 that perform operations for or a method of predicting PCa DECIPHER risk score, or classifying PCa tumors on MRI imagery, including by using a machine learning classifier. Thus, the set of circuits 1230, whether implemented in computer 1200 as hardware, firmware, software, and/or a combination thereof may provide means (e.g., hardware, firmware, circuits) for predicting PCa DECIPHER risk score, or classifying PCa tumors on MRI imagery. In different examples, the set of circuits 1230 may be permanently and/or removably attached to computer 1200.

Processor 1202 can be a variety of various processors including dual microprocessor and other multi-processor architectures. Processor 1202 may be configured to perform steps of methods claimed and described herein. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, or a memory stick. Furthermore, disk 1206 may include optical drives like a CD-ROM or a digital video ROM drive (DVD ROM). Memory 1204 can store processes 1214 or data 1217, for example. Data 1217 may, in one embodiment, include digitized radiological images, including MRI (e.g. mpMRI, bpMRI) images of tissue demonstrating PCa. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, circuits, logics, and peripherals using other buses that are not illustrated (e.g., PCIE, SATA, Infiniband, 1394, USB, Ethernet).

Computer 1200 may interact with input/output devices via I/O interfaces 1218 and input/output ports 1210. Input/output devices can include, but are not limited to, MRI systems, CT systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network. Through the network, computer 1200 may be logically connected to remote computers. The networks with which computer 1200 may interact include, but are not limited to, a local area network (LAN), a wide area network (WAN), or other networks, including the cloud.

Examples herein can include subject matter such as an apparatus, an MRI system, a CT system, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting PCa DECIPHER score, according to embodiments and examples described.

Example 1 is a non-transitory computer-readable storage device storing computer-executable instructions that when executed cause a processor to perform operations, the operations comprising: accessing a radiological image of a region of interest (ROI) demonstrating prostate cancer (PCa), where the ROI includes a tumoral region, where the image is associated with a patient; segmenting the tumoral region represented in the image; extracting a set of radiomic features from the segmented tumoral region; providing the set of radiomic features to a machine learning classifier trained to predict DECIPHER risk group based on the set of radiomic features; receiving, from the machine learning classifier, a probability that the patient is a member of a first DECIPHER risk group; classifying the patient as a member of a first DECIPHER risk group or a second, different DECIPHER risk group based, at least in part, on the probability; and displaying the classification.

Example 2 comprises the subject matter of any variation of any of example(s) 1, where the radiological image is a bi-parametric magnetic resonance imaging (bpMRI) image, the bpMRI image including a T2W MRI image and an apparent diffusion coefficient (ADC) map of the ROI.

Example 3 comprises the subject matter of any variation of any of example(s) 1-2, where the set of radiomic features includes at least one ADC co-occurrence of local anisotropic gradient (CoLIAGe) feature, at least one ADC Laws features, at least one ADC Gabor feature, and at least one T2WI CoLIAGe feature.

Example 4 comprises the subject matter of any variation of any of example(s) 1-3, where the set of radiomic features includes fifteen radiomic features.

Example 5 comprises the subject matter of any variation of any of example(s) 1-4, where the machine learning classifier is a logistic regression model classifier.

Example 6 comprises the subject matter of any variation of any of example(s) 1-5, where the first DECIPHER risk group is a DECIPHER low-risk group or a DECIPHER low/intermediate-risk group, and where the second, different DECIPHER risk group is a DECIPHER high-risk group.

Example 7 comprises the subject matter of any variation of any of example(s) 1-6, the operations further comprising training the machine learning classifier.

Example 8 comprises the subject matter of any variation of any of example(s) 1-7, where training the machine learning classifier comprises: accessing a first dataset, where the first dataset includes a plurality of pre-operative bi-parametric magnetic resonance imaging (bpMRI) images of tissue demonstrating PCa in patients who underwent radical prostatectomy (RP) followed by DECIPHER tests, where a bpMRI image includes a T2W MRI image of a region of tissue demonstrating PCa, and an ADC map of the region of tissue, where the first dataset further includes, for each bpMRI image, a hematoxylin and eosin (H&E) stained image of the region of tissue represented in the bpMRI image, where the DECIPHER risk group of each patient is known, where the first dataset includes a low/intermediate DECIPHER risk group, and a high DECIPHER risk group; co-registering the bpMRI imagery with the corresponding H&E imagery; extracting a set of radiomic features from the first dataset, where, for each member of the plurality of pre-operative bpMRI images, the set of radiomic features includes at least one radiomic feature extracted from a T2WI image, and at least one radiomic feature extracted from an ADC map; dividing the first dataset into a training set and disjoint, testing set, where the training set and the testing set include equal numbers of low/intermediate DECIPHER risk group patients and high DECIPHER risk group patients respectively; and training the machine learning classifier using the training set.

Example 9 comprises the subject matter of any variation of any of example(s) 1-8, where training the machine learning classifier comprises training the machine learning classifier with elastic-net regularization via a 5-fold cross validation approach.

Example 10 comprises the subject matter of any variation of any of example(s) 1-9, where extracting the set of radiomic features includes selecting the N most discriminative radiomic features, N being a positive integer.

Example 11 comprises the subject matter of any variation of any of example(s) 1-10, where the N most discriminative radiomic features are selected using a Pearson's correlation coefficient feature selection approach.

Example 12 comprises the subject matter of any variation of any of example(s) 1-11, where the N most discriminative radiomic features are selected simultaneously with training the machine learning classifier.

Example 13 comprises the subject matter of any variation of any of example(s) 1-12, the operations further comprising testing the machine learning classifier on the testing set.

Example 14 comprises the subject matter of any variation of any of example(s) 1-13, the operations further comprising: generating a personalized treatment plan based, at least in part, on the classification; and displaying the personalized treatment plan.

Example 15 is an apparatus comprising: a processor; a memory configured to store a bi-parametric magnetic resonance imaging (bpMRI) image associated with a patient, where the image includes a region of interest (ROI) demonstrating prostate cancer (PCa) pathology, the bpMRI image having a plurality of pixels, a pixel having an intensity, the bpMRI image comprising a T2W MRI image and an apparent diffusion coefficient (ADC) map; an input/output (I/O) interface; a set of circuits; and an interface that connects the processor, the memory, the I/O interface, and the set of circuits, the set of circuits comprising: an image acquisition circuit configured to: access the bpMRI image; a tumor segmentation circuit configured to: segment a tumoral region represented in the bpMRI image, where segmenting the tumoral region includes defining a tumoral boundary; a radiomic feature circuit configured to: extract a set of radiomic features from the tumoral region represented in the bpMRI image, where the set of radiomic features includes at least one ADC co-occurrence of local anisotropic gradient (CoLIAGe) feature, at least one ADC Laws features, at least one ADC Gabor feature, and at least one T2WI CoLIAGe feature; a DECIPHER risk group prediction circuit configured to: compute a probability that the patient associated with the image is a member of a first DECIPHER risk group, or a member of a second, different DECIPHER risk group, based on the set of radiomic features; generate a classification of the patient as a member of the first DECIPHER risk group, or a member of the second, different DECIPHER risk group based, at least in part, on the probability; and a display circuit configured to display the classification.

Example 16 comprises the subject matter of any variation of any of example(s) 15, where the set of radiomic features includes fifteen radiomic features.

Example 17 comprises the subject matter of any variation of any of example(s) 15-16, where the DECIPHER risk group prediction circuit is configured to compute the probability or generate the classification using a logistic regression model machine learning approach.

Example 18 comprises the subject matter of any variation of any of example(s) 15-17, where the set of circuits further comprises: a PCa personalized treatment plan circuit configured to: generate a personalized treatment plan based, at least in part, on the classification; and where the display circuit is further configured to display the personalized treatment plan.

Example 19 comprises the subject matter of any variation of any of example(s) 15-18, where the set of circuits further comprises: a training and testing circuit configured to: train the DECIPHER risk group prediction circuit on a training cohort; and optionally test the DECIPHER risk group prediction circuit on a testing cohort.

Example 20 comprises a machine readable storage device that stores instructions for execution by a processor to perform any of the described operations of examples 1-19.

Example 21 comprises an apparatus comprising: a memory; and one or more processors configured to: perform any of the described operations of examples 1-19.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed cause a processor to perform operations, the operations comprising:
    accessing a radiological image of a region of interest (ROI) demonstrating prostate cancer (PCa), where the ROI includes a tumoral region, where the image is associated with a patient;
    segmenting the tumoral region represented in the image;
    extracting a set of radiomic features from the segmented tumoral region;
    providing the set of radiomic features to a machine learning classifier trained to predict DECIPHER risk group based on the set of radiomic features;
    receiving, from the machine learning classifier, a probability that the patient is a member of a first DECIPHER risk group;
    classifying the patient as a member of a first DECIPHER risk group or a second, different DECIPHER risk group based, at least in part, on the probability; and
    displaying the classification,
    where the radiological image is a bi-parametric magnetic resonance imaging (bpMRI) image, the bpMRI image including a T2W MRI image and an apparent diffusion coefficient (ADC) map of the ROI, and
    where the set of radiomic features includes at least one ADC co-occurrence of local anisotropic gradient (CoLIAGe) feature, at least one ADC Laws features, at least one ADC Gabor feature, and at least one T2WI CoLIAGe feature.

2. The non-transitory computer-readable storage device of claim 1, where the set of radiomic features includes fifteen radiomic features.

3. The non-transitory computer-readable storage device of claim 1, where the machine learning classifier is a logistic regression model classifier.

4. The non-transitory computer-readable storage device of claim 1, where the first DECIPHER risk group is a DECIPHER low-risk group or a DECIPHER low/intermediate-risk group, and where the second, different DECIPHER risk group is a DECIPHER high-risk group.

5. The non-transitory computer-readable storage device of claim 1, the operations further comprising training the machine learning classifier.

6. The non-transitory computer-readable storage device of claim 1, the operations further comprising:
    generating a personalized treatment plan based, at least in part, on the classification; and
    displaying the personalized treatment plan.

7. The non-transitory computer-readable storage device of claim 5, where training the machine learning classifier comprises:
    accessing a first dataset, where the first dataset includes a plurality of pre-operative bi-parametric magnetic resonance imaging (bpMRI) images of tissue demonstrating PCa in patients who underwent radical prostatectomy (RP) followed by DECIPHER tests, where a bpMRI image includes a T2W MRI image of a region of tissue demonstrating PCa, and an ADC map of the region of tissue, where the first dataset further includes, for each bpMRI image, a hematoxylin and eosin (H&E) stained image of the region of tissue represented in the bpMRI image, where the DECIPHER risk group of each patient is known, where the first dataset includes a low/intermediate DECIPHER risk group, and a high DECIPHER risk group;

co-registering the bpMRI imagery with the corresponding H&E imagery;
extracting a set of radiomic features from the first dataset, where, for each member of the plurality of pre-operative bpMRI images, the set of radiomic features includes at least one radiomic feature extracted from a T2WI image, and at least one radiomic feature extracted from an ADC map;
dividing the first dataset into a training set and disjoint, testing set, where the training set and the testing set include equal numbers of low/intermediate DECIPHER risk group patients and high DECIPHER risk group patients respectively; and
training the machine learning classifier using the training set.

8. The non-transitory computer-readable storage device of claim 7, where training the machine learning classifier comprises training the machine learning classifier with elastic-net regularization via a 5-fold cross validation approach.

9. The non-transitory computer-readable storage device of claim 7, where extracting the set of radiomic features includes selecting the N most discriminative radiomic features, N being a positive integer.

10. The non-transitory computer-readable storage device of claim 7, the operations further comprising testing the machine learning classifier on the testing set.

11. The non-transitory computer-readable storage device of claim 9, where the N most discriminative radiomic features are selected using a Pearson's correlation coefficient feature selection approach.

12. The non-transitory computer-readable storage device of claim 9, where the N most discriminative radiomic features are selected simultaneously with training the machine learning classifier.

13. An apparatus comprising:
a processor;
a memory configured to store a bi-parametric magnetic resonance imaging (bpMRI) image associated with a patient, where the image includes a region of interest (ROI) demonstrating prostate cancer (PCa) pathology, the bpMRI image having a plurality of pixels, a pixel having an intensity, the bpMRI image comprising a T2 W MRI image and an apparent diffusion coefficient (ADC) map;
an input/output (I/O) interface;
a set of circuits; and
an interface that connects the processor, the memory, the I/O interface, and the set of circuits, the set of circuits comprising:
an image acquisition circuit configured to:
access the bpMRI image;
a tumor segmentation circuit configured to:
segment a tumoral region represented in the bpMRI image, where segmenting the tumoral region includes defining a tumoral boundary;
a radiomic feature circuit configured to:
extract a set of radiomic features from the tumoral region represented in the bpMRI image, where the set of radiomic features includes at least one ADC co-occurrence of local anisotropic gradient (CoLIAGe) feature, at least one ADC Laws features, at least one ADC Gabor feature, and at least one T2WI CoLIAGe feature;
a DECIPHER risk group prediction circuit configured to:
compute a probability that the patient associated with the image is a member of a first DECIPHER risk group, or a member of a second, different DECIPHER risk group, based on the set of radiomic features;
generate a classification of the patient as a member of the first DECIPHER risk group, or a member of the second, different DECIPHER risk group based, at least in part, on the probability; and
a display circuit configured to display the classification.

14. The apparatus of claim 13, where the set of radiomic features includes fifteen radiomic features.

15. The apparatus of claim 13, where the DECIPHER risk group prediction circuit is configured to compute the probability or generate the classification using a logistic regression model machine learning approach.

16. The apparatus of claim 13, where the set of circuits further comprises:
a PCa personalized treatment plan circuit configured to:
generate a personalized treatment plan based, at least in part, on the classification; and
where the display circuit is further configured to display the personalized treatment plan.

17. The apparatus of claim 13, where the set of circuits further comprises:
a training and testing circuit configured to:
train the DECIPHER risk group prediction circuit on a training cohort; and optionally
test the DECIPHER risk group prediction circuit on a testing cohort.

18. A non-transitory computer-readable storage device storing computer-executable instructions that when executed cause a processor to perform operations, the operations comprising:
accessing a bi-parametric magnetic resonance imaging (bpMRI) image of a region of interest (ROI) demonstrating prostate cancer (PCa), where the ROI includes a tumoral region, where the bpMRI image is associated with a patient, the bpMRI image including a T2 W MRI image and an apparent diffusion coefficient (ADC) map of the ROI;
segmenting the tumoral region represented in the bpMRI image;
extracting a set of fifteen radiomic features from the segmented tumoral region, where the set of fifteen radiomic features includes at least one ADC co-occurrence of local anisotropic gradient (CoLIAGe) feature, at least one ADC Laws features, at least one ADC Gabor feature, and at least one T2WI CoLIAGe feature;
providing the set of radiomic features to a logistic regression model machine learning classifier trained to predict DECIPHER risk group based on the set of radiomic features;
receiving, from the machine learning classifier, a probability that the patient is a member of a first DECIPHER risk group;
classifying the patient as a member of the first DECIPHER risk group or a second, different DECIPHER risk group based, at least in part, on the probability, where the first DECIPHER risk group is a DECIPHER low/intermediate risk group, and where the second DECIPHER risk group a DECIPHER high-risk group; and
displaying the classification and optionally displaying the probability, the set of radiomic features, or the bpMRI image.

* * * * *

UNITED STATES PATENT AND TRADEMARK OFFICE
CERTIFICATE OF CORRECTION

PATENT NO. : 11,017,896 B2
APPLICATION NO. : 16/395922
DATED : May 25, 2021
INVENTOR(S) : Anant Madabhushi et al.

It is certified that error appears in the above-identified patent and that said Letters Patent is hereby corrected as shown below:

In the Specification

Column 1, Lines 14 through 24; please replace "This invention was made with government support under the grant(s) 1U24CA199374-01, R01CA202752-01AI R01CA208236-01AI, ROI CA216579-01AI, ROI CA220581-01AI, 1 C06 RR12463-01, and VA IBX004121A awarded by the National Institutes of Health. Also awards W81XWH-15-I-0558, W81XWH-16-I-0329, and W81XWH-17-PCRP-IDA awarded by the Department of Defense. The government has certain rights in the invention." with --This invention was made with government support under the grant(s) CA199374, CA202752, CA208236, CA216579, CA220581, and RR012463 awarded by the National Institutes of Health; grants W81XWH-15-I-0558, W81XWH-16-I-0329, and W81XWH-18-1-0524 awarded by the Department of Defense; and grant IBX004121A awarded by the United States Department of Veterans Affairs. The government has certain rights in the invention.--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*